United States Patent [19]

Shipko

[11] 4,037,277
[45] July 26, 1977

[54] SURGICAL TOOL

[75] Inventor: Frederick J. Shipko, Spring Church, Pa.

[73] Assignee: Coratomic Inc., Indiana, Pa.

[21] Appl. No.: 718,794

[22] Filed: Aug. 30, 1976

[51] Int. Cl.² .................. B25F 1/00; B23P 19/02; B25B 13/48
[52] U.S. Cl. ........................... 7/1 G; 29/235; 81/71
[58] Field of Search .............. 7/1 R, 1 G; 81/71; 29/235, 280

[56] References Cited

U.S. PATENT DOCUMENTS

| 2,998,644 | 9/1961 | Thill | 29/280 X |
|---|---|---|---|
| 3,289,286 | 12/1966 | Belanger | 29/235 |
| 3,742,533 | 7/1973 | Brunette | 7/1 G |
| 3,884,282 | 5/1975 | Dobrosielski | 81/125 X |

*Primary Examiner*—James L. Jones, Jr.
*Assistant Examiner*—James G. Smith
*Attorney, Agent, or Firm*—Hymen Diamond

[57] ABSTRACT

A surgical tool for use in implanting a heart pacer. The tool includes a handle from whose one end an Allen wrench extends and in whose other end an O-ring plug having a stem is removably held by the stem. The wrench serves to screw an Allen-head set screw into the pacer to secure the terminal of the catheter which connects the pacer to the heart electrically. The plug seals the hole in which the set screw is inserted preventing electrical leakage by reason of penetration of body fluids to the terminal. The stem is removed from the plug and may serve to seal the suture hole in the pacer when the pacer is not sutured in place.

5 Claims, 8 Drawing Figures

SURGICAL TOOL

BACKGROUND OF THE INVENTION

This invention relates to the art of surgical tools and has particular relationship to tools for use in the implanting of a heart pacer. A typical heart pacer is described in Purdy, et al, U.S. Pat. No. 3,866,616. Such a pacer is implanted in the body of the host, in the case of a human being, in the chest or abdomen. The heart pacer includes an electrical circuit for producing electrical pulses. This circit is electrically connected to the heart through a catheter which has a terminal (or, in the case of a bi-polar circuit, a pair of terminals) that is inserted into a socket which is connected to the electrical circuit. The terminal is secured by a set screw screwed into the heart pacer laterally of the socket.

Surgeons who implant the pacers have in general followed the practice of screwing the set tightly into the pacer so that its tip engages, and becomes cold welded to, the terminal. This practice alone has not proven entirely satisfactory. It has been found that there is electrical leakage through body fluids which contact the terminal directly and also through the set screw. To suppress this electrical leakage some surgeons have adopted the practice of plugging the opening in which the set screw is inserted, and which provides access to the body fluids, with a silicone-rubber cement during the implantation. This has not proven satisfactory. A preferred practice is to plug the opening with a silicone-rubber plug from whose periphery O-rings extend. The set screw is screwed in and the plug is plugged in during the implantation and this invention concerns itself with a tool for carrying out this operation.

In accordance with prior art practice, the surgeon carried out this operation with the aid of a hemostat or like instrument or with his fingers. With this practice the plug was not properly seated to produce an effective seal in the opening. At times the plug, being very small, was lost in the operating room or could even be left in the patient.

It is an object of this invention to overcome the difficulties and disavantages of the prior art and to provide a tool both for screwing in the set screw of a heart pacer and for effectively sealing the set screw and the terminal of the pacer against penetration of body fluids during implantation.

SUMMARY OF THE INVENTION

In accordance with this invention, a tool is provided comprising a handle, typically of NYLON or the like, having a wrench extending from one end and a plug for sealing the set screw removably held in the opposite end. A stem extends from the plug and the stem serves to support the plug in an opening in the handle. By rotation of the handle, the wrench serves to screw the set screw into the heart pacer so that it engages the catheter terminal. The handle also serves to insert the plug into the opening to seal the set screw, and effectively prevent electrical leakage through body fluids from the cavity above the set screw after implanting the pacer. The plug is replaceable in the handle.

BRIEF DESCRIPTION OF THE DRAWING

For a better understanding of this invention, both as to its organization and as to its method of operation, together with additional objects and advantages thereof, reference is made to the following description taken in connection with the accompanying drawings, in which:

FIG. 6 shows the heart pacer to scale and FIGS. 7 and 8 show the heart pacer to half scale (2 inches on the drawing = 1 inch of the actual pacer). The dimensions shown in FIGS. 1 through 5 and the scale adopted in FIGS. 6, 7 and 8 are included for the purpose of aiding those skilled in the art in the practice of this invention, as required by 35 USC 112, and not with any intention of in any way limiting this invention.

DETAILED DESCRIPTION OF EMBODIMENT

Figure 1:
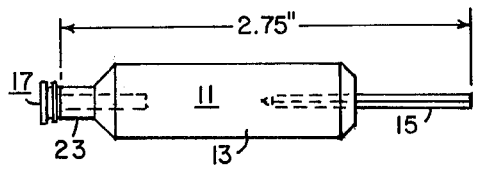
FIG. 1 is a view in side elevation of a surgical tool in accordance with this invention.
Figure 2:
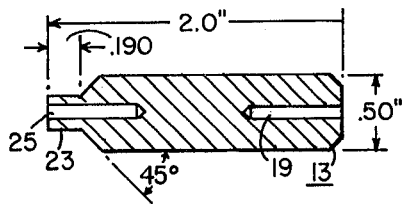
FIG. 2 is a view, in longitudinal section of the handle of the tool shown in FIG. 1.
Figure 3:
FIG. 3 is a view in end elevation of the handle.
Figure 5:
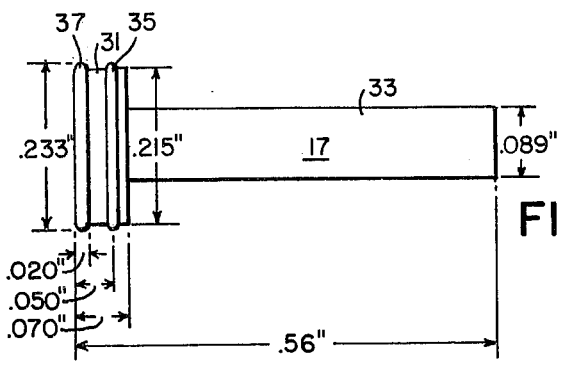
FIG. 5 is a view in side elevation enlarged of the plug and stem of the tool shown in FIG. 1.
Figure 4:
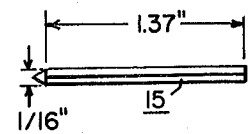
FIG. 4 is a view in side elevation of the wrench of the tool shown in FIG. 1.

The invention shown in FIGS. 1 through 5 is a surgical tool 11 including a handle 13 of cylindrical transverse cross section, a wrench 15 and a plug unit 17. The handle 13 has an axial opening 19 at one end. The wrench 15 is of the Allen-head type and is of hexagonal cross section. The wrench 15 is dimensioned relative to the opening 19 (FIGS. 3 and 4) so that it may be forced into the opening 19 and secured therein. At its opposite end the handle has a sloping shoulder from which a neck 23 extends. An axial opening 25 extends through the neck 23 into the body of the handle proper.

The plug unit 17 (FIG. 5) includes a circularly cylindrical plug 31 from which a stem 33 of circular transverse section extends axially. The plug 31 has an axially external circular protuberance 35 and an axially internal circular protuberance 37. The plug unit typically is composed of about 90% silicone rubber (typically Dow Corning MDX 4-4515) and about 10% barium sulfate and is opaque to X-ray radiation. This enables the surgeon to determine if the plug 31 is properly seated in the opening by means of X-ray exposure. The protuberances 35 and 37 essentially are O-rings which when engaged firmly with an encircling surface form a fluid-tight seal. The stem 33 is dimensioned so that when it is inserted in the opening 25, it fits snugly but removably in the opening.

Figure 6:
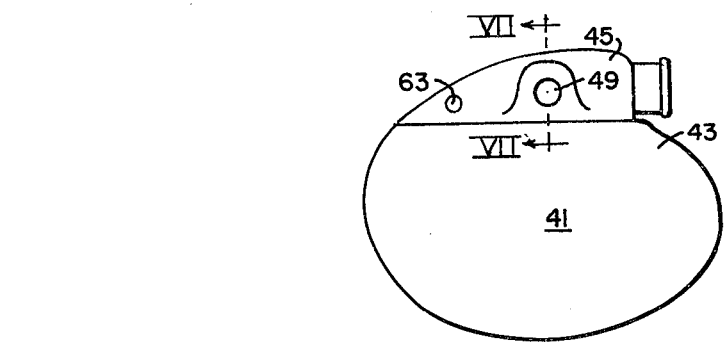
FIG. 6 is a view in side elevation of a heart pacer in whose implanting the tool shown in FIG. 1 is used.
Figure 7:
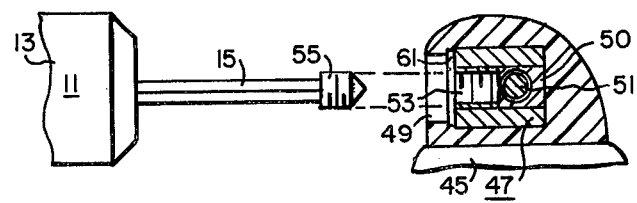
FIG. 7 is a fragmental exploded view illustrating a first step in the practice of this invention and showing enlarged in section taken along line VII-VII of FIG. 6, the portion of the pacer involved in the practice of this invention and the associated portion of the tool shown in FIG. 1
Figure 8:
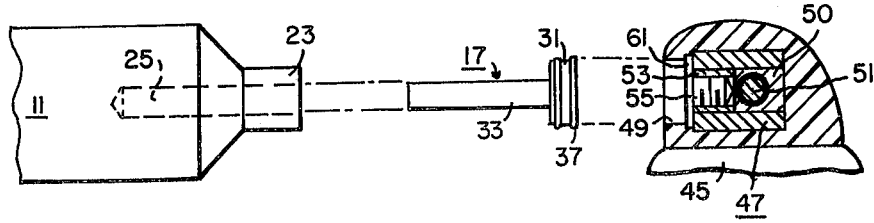
FIG. 8 is a like fragmental exploded view illustrating a second and final step in the practice of this invention.

FIGS. 6, 7 and 8 disclose a heart pacer 41 generally similar to that disclosed in Purdy, et al, patent. The pacer 41 is of generally ellipsoidal or ovaloidal form and has a container 43 of a metal such as titanium, which is not rejected by human tissue, and a head or top 45 composed of an insulator, such as EPOXY resin. Within the top 45 there is a terminal block 47(FIGS. 7 and 8) accessible through a lateral opening 49 in the top. The terminal block 47 is connected to the input and output (connections not shown) of the electrical circuit (not shown) as described in Purdy, et al, patent. The terminal block 47 has a socket for receiving the terminal or pin 51 which extends from the catheter (not shown). A threaded sleeve 53 extends between the opening 49 and the socket 50. To hold the terminal 51 a set screw 55 (FIG 7) with an Allen head is screwed tightly into the sleeve 53. For this purpose the set screw 55 is mounted on the end of the wrench 15. The screw 55 is thrust into the sleeve 53 and screwed in by turning the handle 13. After the screw 55 is screwed into the sleeve 53, the screw is sealed by the plug 31 which is thrust into the opening 49 with the handle 13, as shown in FIG. 8, and secured therein.

In the use of the tool 11 the wrench 15 serves to screw the set screw 55 into the sleeve 53 so that the set screw firmly engages and holds the catheter terminal 51. With the handle the plug 31 is then thrust into the set-screw opening 49 so that the face of the plug firmly engages the (end of the terminal block) and the protrusion 37 seats in the extended portion 61 of the opening 49. The protrusion 35 is compressed against the wall of 49 and seals the opening essentially operating like an O-ring. The protrusion 37 also engages the wall of the opening 61 and serves as an additional seal. The handle 13 and plug 31 are then turned a full revolution (or several revolutions) so that the plug 31 is firmly seated in slot 61. The handle 13 is then removed and the stem 33 is severed from the plug 31. A silicone-rubber cement may be applied to the outside surface of the plug 31 which is recessed in the opening 49. If the pacer 41 is not sutured to adjoining tissue, the suture opening 63 in the pacer 41 may be closed by inserting and securing the severed stem in this opening. Otherwise, the stem is discarded.

While a preferred embodiment of this invention has been disclosed herein, many modifications thereof are feasible. This invention is not to be restricted except insofar as is necessitated by the spirit of the prior art.

I claim:

1. In combination a heart pacer having a socket for receiving a terminal for effecting an electrical connection to said heart, and also having an opening extending from said socket laterally of said socket and a thread in said opening for receiving a set screw to secure said terminal to said socket, and a surgical tool for use in the implanting said heart pacer in the heart of a host, the said tool comprising a handle, a wrench for screwing a set screw into said thread for securing said terminal in said socket, secured in one end of said handle, and a plug for sealing said opening, said plug having a stem and being removably held by said stem in the opposite end of said handle.

2. The combination of claim 1 wherein the handle of the tool has a neck at the end in which the plug is removably held, said neck having a transverse cross-sectional dimension approximately the same as the transverse cross-sectional dimension of the plug and of the entrance to the opening in the heart pacer.

3. In combination a heart pacer having a terminal recessed in a recess in said pacer to be sealed against penetration of body fluid by a plug forming an O-ring seal with the wall of said recess and having a stem, and a surgical tool for use in implanting, said heart pacer in the heart of a host, the said tool includng a handle, the end of said handle removably engaging said stem, so that by use of the handle the plug is forced into said recess and turned to seal said opening, the said end of said handle having a neck within which the stem of said plug is removably engaged, said neck having a transverse cross-sectional dimension approximately the same as the transverse cross-sectional dimension of said plug and of said recess, enabling insertion and turning of said plug in said recess.

4. In combination a heart pacer having a socket for receiving a terminal for effecting electrical connection to said heart, the said pacer also having an opening extending from said socket laterally of said socket, said opening having a thread, a set screw to be screwed into said thread to secure said terminal in said socket and the said opening to be sealed by a plug to be compressed against the wall of said opening to form a seal, said plug, prior to insertion in said opening extending from a stem and a surgical tool for use in implanting said heart pacer in the heart of a host, the said tool comprising a handle, a wrench, for screwing said set screw into said opening, secured in one end of said handle, said other end of said handle being formed to removably receive said stem of said plug and to hold said plug by said stem, whereby by operation of said handle said plug is forced into said opening to seal said opening.

5. The combination of Claim 4 wherein the handle is formed with an attenuated neck into which the stem of the plug is inserted, said neck facilitating the forcing of the plug into the opening by manipulation of the handle.

* * * * *